United States Patent [19]

Ponroy

[11] Patent Number: 5,853,747
[45] Date of Patent: Dec. 29, 1998

[54] THERAPEUTIC AND DIETETIC USES OF A BRAIN PHOSPHOLIPID-BASED COMPLEX

[75] Inventor: Yves Ponroy, Versailles, France

[73] Assignee: Institut De Recherche Biologique, France

[21] Appl. No.: 617,806

[22] PCT Filed: Jun. 13, 1995

[86] PCT No.: PCT/FR95/00771

§ 371 Date: Feb. 27, 1996

§ 102(e) Date: Feb. 27, 1996

[87] PCT Pub. No.: WO96/00077

PCT Pub. Date: Jan. 4, 1996

[30] Foreign Application Priority Data

Jun. 27, 1994 [FR] France .................................. 94 07867

[51] Int. Cl.$^6$ .............................. A61K 35/30; C12P 23/00
[52] U.S. Cl. .......................... 424/439; 424/520; 424/570; 435/1.1; 435/67
[58] Field of Search ..................... 424/439, 520, 424/570; 435/1.1, 67

[56] References Cited

U.S. PATENT DOCUMENTS 4,963,527 10/1990 Bombardelli .
5,562,913 10/1996 Horrobin .

OTHER PUBLICATIONS

Lehninger et al. *Principles of Biochemistry* 2nd ed., 1993, pp. 341, 344, 886.
Scandalios, *Physiological Genetics*, 1979, p. 40–41.

*Primary Examiner*—Ponnathapura Achutamurthy
*Assistant Examiner*—Phuong T. Bui
*Attorney, Agent, or Firm*—Bierman, Muserlian and Lucas

[57] ABSTRACT

The therapeutic or dietetic use of a preparation based on phospholipids extracted from pig brains for treating aging disorders consisting of memory disorders, attention disorders, intellectual efficacy disorders, humor and affectivity disorders, and thinking difficulty in a human is disclosed. The purified brain phospholipids are used alone or in combination with carriers and diluents enabling oral delivery.

6 Claims, No Drawings

THERAPEUTIC AND DIETETIC USES OF A BRAIN PHOSPHOLIPID-BASED COMPLEX

The present invention relates to novel therapeutic and dietetic uses of a mixture of animal phospholipids.

More particularly the present invention has as a subject matter the use of a mixture of phospholipids extracted from mammalian brains, for the realization of compositions which are used in the therapeutic or nutritional domain.

Specifically it has as a subject matter the therapeutic or nutritional use of a preparation based on brain phospholipids extracted from pig brains for alleviating or delaying aging phenomenas and particularly the mental deterioration, hypoxia and cerebral aging.

The physiological aging is accompanied at the brain level of:

- a decrease in the rate of phospholipids with an occurrence of lysoderivatives, and thus the ratio cholesterol/phospholipid is increased, which leads to a decrease of the membrane fluidity (G. CALDERINI, Phospholipids in the nervous system Vol.2 (1985)11–18- Raven Press).
- moreover, the membrane phospholipids suffer in the course of the aging from the peroxidation phenomena which worsen the biological activity of this polyunsaturated molecules (C.DEBY- La biochimie de l'oxygène- La Recherche 22 (1991) 57–64)
- in the animals, it has been in effect observed an increase of the brain phospholipase rate during aging and a decrease of the synthesis capacity of phospholipids (A. GAITI- Phospholipids in the nervous system Vol.2 (1985) 155–161- Raven Press).
- finally, one knows that in the aged subject, a decrease in the activity of the delta-6-desaturase is noted, which allows the transformation of essential fatty acids (18:2 n-6 et 18:3 n-3) in higher fatty acids and particularly in DHA (22:6 n-3) (JM BOURRE (1990) 25 354–356)

In the Alzheimer's disease, one is witnessing phenomenas of the same nature but not totally identical.

- intracellular lipochrome pigments are formed which contain inter alia triglycerides, cephalins, sphingomyelins and oxidized polyunsaturated fatty acids (H. DABADIE - Cahiers Nut. Diet. XXII (1987) 51–53). It may be molecules of brain phospholipids which have been damaged.
- the deterioration of the metabolism of phospholipids in the Alzheimer's disease, as the membrane deteriorates, have moreover been evidenced by G.ZUBENKO (Brain Research 385 (5) (1986) 115–121).
- one also have found in the diseased brains, an important amount of phospho mono and di-esters, what may mean either a lysis, either a regenerating effort of the membrane phospholipids. (J. W PETTEGREW-J. Neuropath.Exp.Neurology (1987) 46 419–430).
- X-rays studies diffraction show a disorganization of the myelin due to a peroxidation of the unsaturated lipids (L.S CHIABiochim Biophys.Acta 775 (1984)308–312)
- various clinical studies in double blind tests against placebo, have shown the efficacy of the brain phosphatidylserin at the dosage of 300 mg/day (L. AMADUCCI-Ann.NY Acad. Sci. 640 (1991) 245–249).

In brain ischemia and states of experimental hypoxia, one notes a marked increase of the pool of free fatty acids, and particularly, of the acids of 20:4 and 22:6 type as well as an increase of lysoderivatives and diglycerides. In the same way, several authors stated in increase of the rate of perodidation of unsaturated fatty acids. This accumulation in free fatty acids and oxidized compounds impair the brain functions (R. V. DORMAN (Phospholipids in the nervous system Vol.1 (1982) 123–135).

In other respects, one known for a long time, that brain hypoxia cause a marked decrease of the metabolism of brain phospholipids (D. A. CHTVERIKOV Nature 212 (1966) 1236–1238 et Y. DJORKIN-Nature 212 (1966) 1239–1240)

The entirety of these elements show that mental deteriorations caused by hypoxic states are associated with a deterioration of membrane phospholipids.

One consequently studied the interest of an exogenous supply of brain phospholipids with the intend to regenerate the cell membranes or to curb their deterioration at the time of physiological and pathological processes and to bring at the brain, specific fatty acids and particularly, acids in 20:4 n-6 and 22:6 n-3.

The cerebral phospholipids are characterized by the fact they contain a high percentage of long chain fatty acids, and particularly of the n-3 series. They represent 5% of the brain weight and have a considerable stuctural and metabolic role at the membrane level (Lipids malnutrition and the developing brain, Elsevier 1972).

The preparation contain a mixture of brain phospholipids in physiological proportion such as:

| | |
|---|---|
| phosphatidylcholine | 20 to 30% |
| phosphatidylserine | |
| phosphatidyllinositol | 17 to 25% |
| phosphatidylethanolamine | 30 to 40% |
| sphingomyelin | 6 to 10% |
| plasmalogen (lipidic ether) | 5 to 10% |

The cerebral phospholipids have this in particular that they are constituted of phosphoglycerol bound to two chains of fatty acids through an ester function or an ether function. The phospholipid ethers, also called plasmalogens, represents from 5 to 10% of the whole.

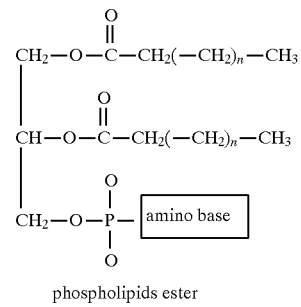

phospholipids ester

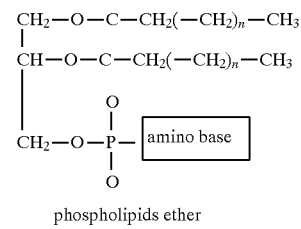

phospholipids ether

The cerebral phospholipids have the distinctive features of being bound to fatty acids the distribution of which is as follows, and the distribution is specific with regard to others phospholipids and particularly with regard to soya phospholipids.

| | | |
|---|---|---|
| arachidonic acid | 20:4 n-6 | 7 to 9% |
| | 22:4 n-6 | 3 to 5% |
| DHA | 22:6 n-3 | 7 to 10% |
| EPA | 20:5 n-3 | <1% |

The applicant have, for this purpose, performed studies with labelled phospholipids, which have shown a preferential migration of the brain phospholipids to the brain after an administration per os.

The applicant has also shown that brain phospholipids rich in long chain polyunsaturated fatty acids, administered orally to mice, set on part to the cerebral level and, particularly, to synapsis membranes.

In other respects, several clinical studies performed in the man in different kinds of cerebral lesions, have confirmed the interest of the use of the brain phospholipids in these indications.

- in 20 cases of brain circulatory insufficiencies, treated with a product which merely contain cerebral phospholipids on the basis of 20 to 40 mg/day during an average of 7 months, it has been observed:
- a clear improvement in 73% of cases based on psychometric tests WESHLER, REY AND BENTON
- the more clear improvements have carried on the memorization and the anxious component which is frequent in these patients.
- the tolerance has been excellent
- in a controlled study versus placebo, with associated pairs, realized in 26 patients suffering from hemiplegia, is may be observed that, after 4 months, the difference is highly significant between the two groups (p $\leq 0,0005$) concerning the amelioration of psychometric tests.
- in a controlled study versus placebo in the treatment of the presenescency in 76 patients which are in average 60 years old, the improvement on subjective tests has been statistically significant after 3 months of treatment, in favour of the brain phospholipids (40 mg/day in two intakes). The best results are observed in the memory disorders, attention disorders and the disorders in the intellectual efficacy as well as those of humour and affectivity. The clinical and biological tolerance has been excellent.

Further it has been carried out a trial for a product associating brain phospholipids, natural anti-oxidizer and fish oil in aging brain disorders, in 61 subjects. After 3 months of treatment, the experimenters have noticed a clear improvement in 60 to 75% of cases, in the following items on << clinical estimating scale in Geriatrics >> (CESG)

- memory of recent events
- emotional stability
- tiredness
- readiness of mind
- anxiety
- initiative
- depression Clinical tolerance has been excellent.

Finally, an open test in 23 patients which bore psycho-intellectual sequelaes of cranial traumas, treated during 3 months with 30 mg/day of brain phospholipids, has allowed to register a global improvement in the order of 63% in BENTON's test. The memory and resistance to tiredness are the most influenced items.

This consequently demonstrates the interest and the efficacy of preparations based on phospholipids from pig brains due to their high content in essential fatty and of n-3 and n-6 series. It has as a result, an improvement of the disorders which are bound to the brain aging such as fatigability, attention loss or difficulty of ideation.

The phospholipids from pigs' brains are used for therapeutic or nutritional purposes, alone or associated with carriers, diluents or vehicles allowing their administration by per os way or intravenous way.

The content in brains phospholipids varies in very high proportion, ranging from 10 to 500 mg per unit dosage.

This purified brain phospholipids can be used alone or associated. They are optionally intended to the digestive way, but they can also be used by the general way:

- per os in the form of soft gelatine capsules or capsules on the basis of 40 to 400 mg/day of brain phospholipids They can be usefully associated to a natural anti-oxidizer such as vitamin C, vitamin E, β-carotene, radical scavengers such as selenium or cysteine, fish oils rich in EPA and DHA.
- Intravenous in the form of a aqueous suspension or liposomes.

As natural anti-oxidizers, there may be cited ascorbic and its salts, the ascorbyl palmitate and tocopherols.

As a radical scavenger agent, there may be cited sulfur containing derivatives such as cystein, carboxymethyl cystein, diterbutyl paracresol or even potassium metabisulfite.

The phospholipids of pig brains can be used for nutritional purposes in conjunction or admixture with carriers or diluents for alimentary use such as cereal flours, fats, inert carriers, chocolated products or milk derivatives.

The brain phospholipids according to the invention are obtained by sampled in extracting the pig brains of freshly slaughtered animals according to the following conditions:

- pig brains are taken from freshly slaughtered animals coming from breedings exempt from any infectious disease and strictly followed from a sanitary point of view by the veterinary services.
- brains are immediately frozen at −20° C. and preserved at this temperature.
- brains are then brought at a temperature ranging −5° C. to 0° C. before they are passed through an industrial mincer and crushing machines, in order to obtain a liquid paste, the water content of which is about 80%.
- brain paste is transferred to the top of an atomization chamber wherein water is immediately evaporated in a warm air current at 190°/195° C.
- the obtained powder is introduced into a reactor containing a mixture of aliphatic hydrocarbons based on hexane and kept under stirring.
- after filtration, the liquid phase is concentrated in vacuum and give rise to a crude extract.
- the crude extract is then poured in acetone with an alimentary anti oxidizing agent
- the obtained precipitate is filtered under nitrogen pressure
- the collected product is dried in vacuum and contains purified brain phospholipids The following examples illustrate the invention, without limiting it, it in any way:

EXAMPLE I

Soft gelatin capsules of phospholipids from pig brains

| | |
|---|---|
| Brain phospholipids | 200 g |
| Ascorbyl palmitate | 12 g |
| Vitamine E | 60 g |
| Sorbitol | 40 g |
| Calcium gluconate | 25 g |
| Magnesium stearate | 15 g |
| for 1000 soft gelatin capsules | |

EXAMPLE II

Soft gelatin capsules of phospholipids from pig brains

| | |
|---|---|
| Brain phospholipids | 100 g |
| Calcium carbonate | 40 g |
| Magnesium carbonate | 30 g |
| Magnesium phosphate | 30 g |
| Colloidal silica | 25 g |
| Vitamin E | 25 g |
| Talc | 15 g |
| for 1000 soft gelatin capsules | |

EXAMPLE III

Soft gelatin capsules of phospholipids from pig brains

| | |
|---|---|
| Brain phospholipids | 100 g |
| Microcrystaliine cellulose | 50 g |
| Ethyl cellulose | 15 g |
| Corn germ oil | 10 g |
| Tricalcium phosphate | 50 g |
| Talc | 10 g |
| for 1000 soft gelatin capsules | |

EXAMPLE IV

Aqueous suspension of brain phospholipids

| | |
|---|---|
| Brain phospholipids | 10 g |
| Soja lecithin | 5 g |
| Vitamin E | 1 g |
| Purified water ad | 1000 ml |

EXAMPLE V

Alimentary flour based on brain phospholipids

| | |
|---|---|
| Brain phospholipids | 20 g |
| Casein | 5 g |
| Methyl cellulose | 4,5 g |
| Banana flours | 71,5 g |
| Vanillin | 0,5 g |
| for a preparation | |

I claim:

1. A method of treating aging disorders selected from the group consisting of memory disorders, attention disorders, intellectual efficacy disorders, humor and affectivity disorders, comprising orally administering to a human in need thereof brain phospholipids extracted from pig's brains.

2. The method of claim 1 wherein the brain phospholipids also contain at least one member of the group consisting of natural anti-oxidizing agents, anti-radical agents and fish oils rich in eicosapentaenoic acid and docosahexaenoic acid.

3. The method of claim 2 wherein the anti-oxidizing agent is selected from the group consisting of ascorbic acid, tocopherols and β-carotene.

4. The method of claim 1 wherein the brain phospholipids are administered by incorporation into at least one member of the group consisting of cereal flours, milk products, fats and chocolate products.

5. The method of claim 1 wherein the brain phospholipids are orally administered at a dose of 10 to 500 mg of brain phospholipids per unit dosage.

6. The method of claim 1 wherein the brain phospholipids are orally administered at a dose of 40 to 400 mg in two or three times daily.

* * * * *